United States Patent  
Bates et al.

(10) Patent No.: US 8,029,560 B2  
(45) Date of Patent: Oct. 4, 2011

(54) ENHANCED REMODELABLE MATERIALS FOR OCCLUDING BODILY VESSELS

(75) Inventors: Brian L. Bates, Bloomington, IN (US); Ram H. Paul, Bloomington, IN (US); Jacob A. Flagle, New Palestine, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 66 days.

(21) Appl. No.: 12/209,483

(22) Filed: Sep. 12, 2008

(65) Prior Publication Data

US 2009/0069758 A1 Mar. 12, 2009

Related U.S. Application Data

(60) Provisional application No. 60/971,724, filed on Sep. 12, 2007.

(51) Int. Cl.  
*A61F 2/06* (2006.01)

(52) U.S. Cl. ............ 623/1.38; 606/213; 623/23.67

(58) Field of Classification Search ........... 623/1.38; 424/423; 606/198  
See application file for complete search history.

(56) References Cited

U.S. PATENT DOCUMENTS

| | | |
|---|---|---|
| 4,511,653 A | 4/1985 | Play et al. |
| 4,902,508 A | 2/1990 | Badylak |
| 4,956,178 A | 9/1990 | Badylak |
| 5,275,826 A | 1/1994 | Badylak |
| 5,456,693 A | 10/1995 | Conston et al. |
| 5,516,533 A | 5/1996 | Badylak |
| 5,554,389 A | 9/1996 | Badylak |
| 5,676,926 A | 10/1997 | Platzek et al. |
| 5,676,962 A | 10/1997 | Garrido et al. |
| 5,955,110 A | 9/1999 | Patel et al. |
| 5,993,844 A | 11/1999 | Abraham et al. |
| 6,099,567 A | 8/2000 | Badylak |
| 6,200,336 B1 | 3/2001 | Pavcnik et al. |
| 6,206,931 B1 | 3/2001 | Cook et al. |
| 6,375,989 B1 | 4/2002 | Badylak et al. |
| 6,444,229 B2 | 9/2002 | Voytik-Harbin et al. |
| 6,508,833 B2 | 1/2003 | Pavcnik et al. |
| 6,572,873 B1 | 6/2003 | Osman et al. |
| 6,592,566 B2 | 7/2003 | Kipke et al. |
| 6,645,167 B1 | 11/2003 | Whalen, II et al. |
| 2001/0011187 A1 | 8/2001 | Pavcnik et al. |

(Continued)

FOREIGN PATENT DOCUMENTS

WO WO 98/22158 5/1998

(Continued)

OTHER PUBLICATIONS

International Search Report from PCT/US08/76139.

(Continued)

*Primary Examiner* — David H Willse  
*Assistant Examiner* — Tiffany Shipmon  
(74) *Attorney, Agent, or Firm* — Woodard, Emhardt, Moriarty, McNett & Henry LLP

(57) ABSTRACT

Described are methods, devices, and systems for occluding or ablating vascular vessels. Noninvasive procedures can be used to occlude and obliterate the greater saphenous vein, for example in the treatment of varicose vein condition caused by venous valve insufficiency. Further described is the cooperative use of an angiogenic remodelable material with one or more sclerosing agents to cause closure of a targeted bodily vessel.

27 Claims, 3 Drawing Sheets

U.S. PATENT DOCUMENTS

| | | | |
|---|---|---|---|
| 2001/0039450 A1 | 11/2001 | Pavcnik et al. | |
| 2002/0058640 A1 | 5/2002 | Abrams et al. | |
| 2002/0103542 A1* | 8/2002 | Bilbo | 623/23.72 |
| 2002/0168366 A1 | 11/2002 | Stewart et al. | |
| 2003/0013989 A1* | 1/2003 | Obermiller et al. | 600/567 |
| 2003/0051735 A1 | 3/2003 | Pavcnik et al. | |
| 2003/0059372 A1 | 3/2003 | Whalen et al. | |
| 2003/0082224 A1 | 5/2003 | Noujaim et al. | |
| 2004/0087930 A1 | 5/2004 | Whalen et al. | |
| 2004/0097901 A1 | 5/2004 | Whalen et al. | |
| 2004/0254589 A1 | 12/2004 | Darnis et al. | |
| 2005/0060028 A1* | 3/2005 | Horres et al. | 623/1.38 |
| 2005/0155608 A1* | 7/2005 | Pavcnik et al. | 128/831 |
| 2005/0228486 A1 | 10/2005 | Case | |
| 2006/0149309 A1* | 7/2006 | Paul et al. | 606/195 |
| 2006/0161197 A1 | 7/2006 | Paul | |
| 2006/0229669 A1 | 10/2006 | Mirizzi et al. | |
| 2007/0166345 A1* | 7/2007 | Pavcnik et al. | 424/423 |
| 2007/0292472 A1 | 12/2007 | Paul | |
| 2008/0004657 A1* | 1/2008 | Obermiller et al. | 606/213 |
| 2009/0018637 A1 | 1/2009 | Paul | |

FOREIGN PATENT DOCUMENTS

| | | | |
|---|---|---|---|
| WO | WO 98/25637 | | 6/1998 |
| WO | WO 00/32250 | | 6/2000 |
| WO | WO 00/32253 | | 6/2000 |
| WO | WO 2005/020847 | | 3/2005 |
| WO | WO2005/053547 | * | 6/2005 |
| WO | WO 2005/053547 | | 6/2005 |
| WO | WO 2004/103187 | | 2/2006 |
| WO | WO 2006/026412 | | 3/2006 |
| WO | WO 2007/090150 | | 8/2007 |
| WO | WO 2007/090155 | | 8/2007 |
| WO | WO 2007/147127 | | 12/2007 |

OTHER PUBLICATIONS

Written Opinion from PCT/US08/76139.

Heeschen, Christopher et al., "Nicotine stimulates angiogenesis and promotes tumor growth and atherosclerosis," Nature Medicine, vol. 7, No. 7, Jul. 200, pp. 833-839.

Johnson, Chad et al., "Matrix Metalloproteinase-9 Is Required for Adequate Angiogenic Revascularization of Ischemic Tissues: Potential Role in Capillary Branching," Circulation Research 94 (2004) No. 2, pp. 262-268.

* cited by examiner

ENHANCED REMODELABLE MATERIALS FOR OCCLUDING BODILY VESSELS

RELATED APPLICATIONS

This application claims the benefit of U.S. Provisional Patent Application Ser. No. 60/971,724, filed Sep. 12, 2007, entitled Enhanced Remodelable Materials for Occluding Bodily Vessels and Related Methods and Systems, which is hereby incorporated herein in its entirety.

BACKGROUND

The present invention resides generally in the field of devices and methods useful for the deployment of prosthetic devices, and in a particular aspect relates to the deployment of prosthetic devices within the vasculature of a patient to treat complications, such as a varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of one or more sclerosing agents to the lumen of a varicose, or other smaller diameter vein, which induce the vein to collapse and the venous walls to fuse, thereby closing the vein.

In view of this background, the need remains for improved and alternative techniques, devices and systems for affecting the venous system to treat venous conditions. The present invention is addressed to these needs.

SUMMARY OF THE INVENTION

Accordingly, in one aspect, the present invention provides a method for closing a venous vessel that includes the cooperative emplacement of a remodelable material and one or more sclerosive agents within the venous vessel. The method includes injuring a venous wall segment with a sclerosing agent and contacting an angiogenic remodelable material to the injured venous tissue so as to occlude the vein in the treatment of venous valve insufficiency.

In another aspect, the present invention provides a medical product for occluding a venous vessel that includes a remodelable material that is configured for deployment within a venous vessel and that is effective to promote the ingrowth of patient tissue into the lumen of the venous vessel. The remodelable material includes one or more sclerosants that are effective to injure the lining of the venous vessel so as to enhance the ingrowth of patient tissue into the remodelable material and promote occlusion of the venous vessel.

In yet another aspect, the present invention provides a medical product for occluding a bodily vessel that includes one or more sclerosing agents and an angiogenic remodelable material. The sclerosing agents and the remodelable material are configured for conjunctive or cooperative use to enhance closure of the bodily vessel. Advantageous such angiogenic remodelable materials can include extracellular matrix materials, such as porcine small intestine submucosa.

In still yet another aspect, the present invention provides a method for occluding a venous vessel that includes providing a flowable remodelable material and one or more sclerosive agents. The flowable material is configured for placement within a venous vessel and is effective to promote the ingrowth of patient tissue within the lumen of the venous vessel. The sclerosive agents are configured for placement within the venous vessel in conjunction with the provided flowable material and are effective to injure the lining of the venous vessel. The method includes locating the provided flowable material and the provided sclerosive agents within the venous vessel wherein the material and agents cooperate to promote the closure and occlusion of the venous vessel.

In another aspect, the present invention provides a method for treating varicosities associated with venous valve insufficiency comprising providing a sponge form remodelable prosthesis that includes one or more sclerosive agents. The method continues by deploying the provided prosthesis within the greater or lesser saphenous vein of the patient so as to provide closure of the vein and treat varicosities associated with venous valve insufficiency.

In yet another aspect, the present invention provides a medical kit that includes a medical product as discussed herein enclosed in sterile medical packaging.

The present invention provides improved methods, system, and devices for occluding venous and other bodily vessels. Additional embodiments as well as features and advantages of the invention will be apparent from the further descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the invention provide for the treatment of venous valve insufficiency with the cooperative emplacement of a remodelable material and one or more sclerosants within a venous vessel, such as the greater saphenous vein. The method can include injuring a venous wall segment with a sclerosing agent and contacting an angiogenic remodelable material to the injured venous tissue so as to occlude the vein. The angiogenic remodelable material can include an extracellular matrix material, such as a sponge form material or a flowable material, and the sclerosive agent can be contained within the material, such as by soaking, mixing, or containing the sclerosive agent within the material, immediately prior to implantation, if desirable.

Figure 1:
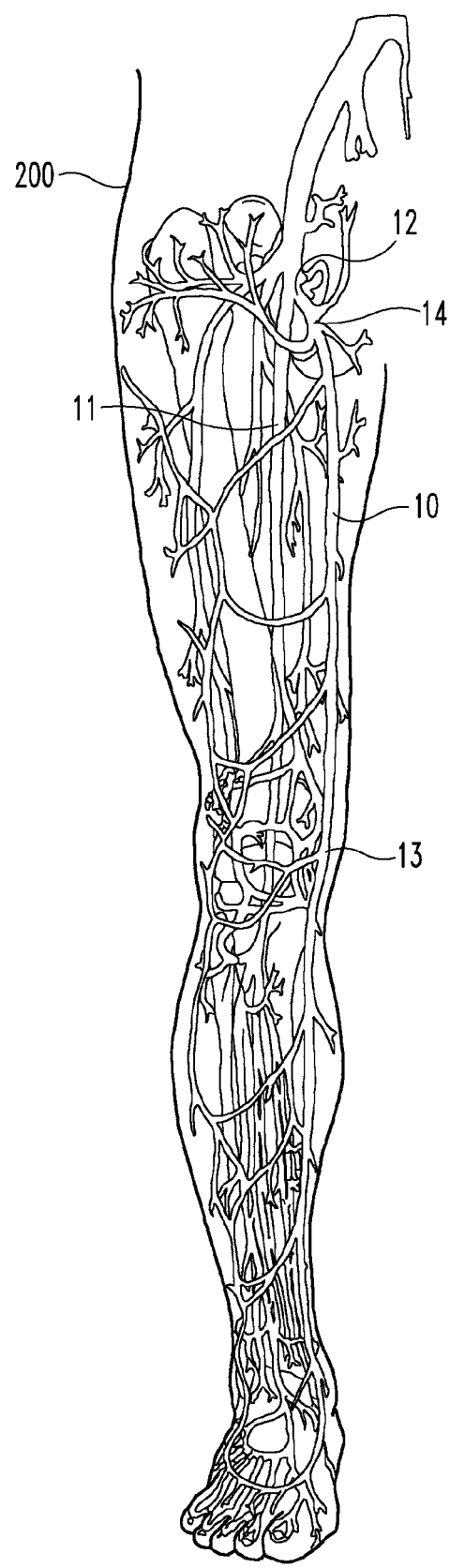
FIG. 1 depicts a human leg showing certain venous structures therein.
Figure 2:
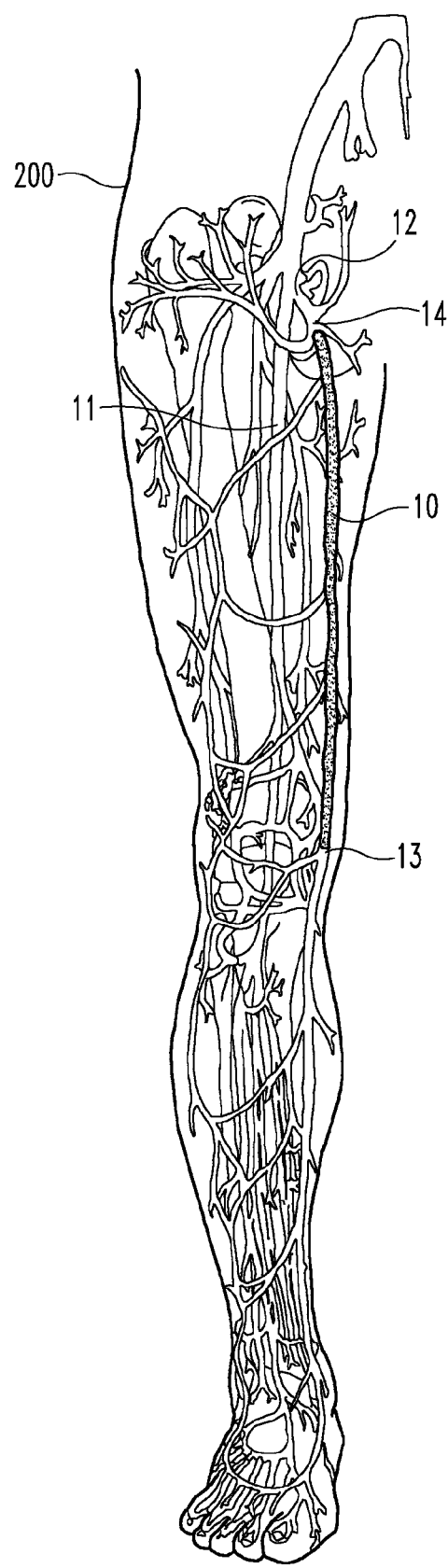
FIG. 2 depicts a human leg showing certain venous structures therein.

With reference now more particularly to the figures, shown in FIG. 1 is a diagram of a human leg showing certain venous structures therein. In particular, shown is human leg 200 having greater saphenous vein 10 and the femoral vein 11 which adjoin at the sapheno-femoral junction 12. In accordance with certain aspects of the invention, greater saphenous vein 10 can be occluded in a region constituting substantially all of the passage between a point 13 occurring near the medial side of the knee to a point 14 occurring prior to the sapheno-femoral junction 12, as illustrated by the shaded area in FIG. 2. Desirably, such occlusion is effective to prevent reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
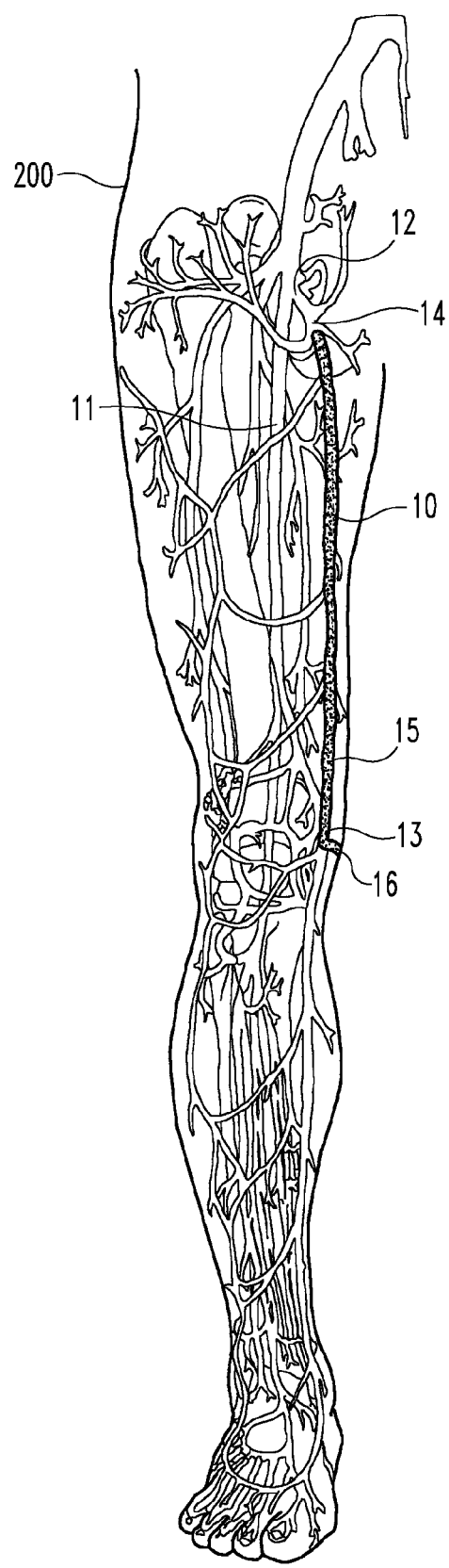
FIG. 3 depicts a human leg having an illustrative occlusion device located in the greater saphenous vein.

With reference now to FIG. 3, occlusion of the passage of the greater saphenous vein occurring between points 13 and 14 can be achieved by cooperatively deploying an occlusive material 15 and one or more sclerosants from point 13 to point 14. In certain embodiments, the occlusive material may include an elongate sponge form material that may include an end portion 16 that traverses the wall of the greater saphenous vein 10. In alternative embodiments, the occlusive material may include a flowable remodelable material that can continuously or intermittently extend between points 13 and 14 within the greater saphenous vein 10. Illustratively, the sclerosive material can be contained within the occlusive material at implantation, or can be emplaced within the vein 10 before, after, or during implantation of the occlusive material.

In an illustrative deployment procedure, percutaneous access to the GSV can be achieved at point 13 using the Seldinger or any other suitable technique. For instance, an access needle can be passed through the skin to access the GSV 10, and a wire guide can be passed through the access needle and into the vein 10. Prior to the deployment of any occlusive or sclerosive material, the wire guide can be used for any number of conventional procedures including catheterization and imaging procedures to locate the sapheno-femoral junction 12, or vein dilation and/or straightening procedures to prepare the vein for an occlusive implant. After any such preliminary procedures that are performed, the wire guide can be used to place a cannulated delivery device within the vein 10. The wire guide can then be removed from the vein 10, thereby providing an open lumen through the cannulated device for delivery of one or more sclerosive agents and occlusive materials, as are discussed herein.

In illustrative embodiments, such as when the occlusive material has low pushability or column strength, e.g. certain sponge form materials, an everting delivery sheath, peel away sheath, or a sheath having a reversible sleeve component can be used to deploy the occlusive device within the vascular vessel 10. In such procedures, the occlusive material and sheath can be delivered using any suitable method, such as over a wire guide or through another cannulated device. In alternative embodiments, such as when a foam material has sufficient column strength, the occluder, optionally containing a sclerosant, can be introduced into the vein and thereafter openly advanced (without a sheath) through the vein to implant the device, over a guide wire if desirable. In still alternative embodiments, such as when percutaneous access is undesirable, the sclerosive agents and certain flowable occlusive materials can be injected at one or more locations between points 13 and 14 within the GSV 10 using one or more needle/syringe combinations until suitable occlusion is achieved. For more information concerning suitable endoluminal delivery techniques, reference can be made, for example to U.S. Pat. Pub. No. 2003/0051735 and/or WO2005/053547.

Turning now to a discussion of occlusive device materials, illustrative such materials can include any suitable biocompatible material. Generally, the occlusion materials may include synthetic materials or reconstituted or naturally-derived collagenous materials. Such biocompatible materials that are at least bioresorbable will provide advantage in embodiments of the invention, with materials that are bioremodelable and promote cellular invasion and ingrowth providing particular advantage. Illustratively, remodelable materials may be used in this context to promote cellular growth within the occlusive materials to promote the closure of an occluded passageway.

Bioremodelable materials of the invention can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the invention will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted of at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the invention will include significant amounts of such interspersed, non-collagenous solids that are readily ascertainable under light microscopic examination. Such non-collagenous solids can constitute a significant percentage of the dry weight of the ECM material in certain embodiments, for example at least about 1%, at least about 3%, and at least about 5% by weight in various embodiments of the invention.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the ECM material within the patient.

Submucosa or other ECM material used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present invention.

Turning now to a discussion of three-dimensionally stable materials, e.g. foam or sponge form materials, that can be used to form occlusive devices, such materials may include any suitable biocompatible material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers or materials, such as hydrogels, gel foam, and/or polyvinyl (alcohol) foam. More preferred sponge compositions will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of closure devices of the invention.

Preferred sources of collagen for forming illustrative sponge matrices include extracellular matrix materials as discussed herein, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, 6,206,931, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials that can be used to form illustrative devices can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in aspects of the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially, such as can be provided by a radial compression device. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming occlusive bodies of the invention can be highly dense, typically having densities of at least about 0.05 g/cm$^3$, preferably in the range of about 0.05 g/cm$^3$ to about 0.2 g/cm$^3$, and more preferably about 0.075 g/cm$^3$ to about 0.2 g/cm$^3$. The compacted sponge matrix can have sufficient column strength to be deployed by passage through needles, catheters, sheaths, or bodily vessels for example by utilizing a push rod or other pusher element (gloved hand) to force the sponge matrix body through the vessel, needle and/or catheter cannula. Expanded sponge densities (dry) will generally be less than the corresponding compacted densities. Typical expanded densities (dry) will range from about 0.01 g/cm$^3$ to about 0.1 g/cm$^3$, more preferably about 0.02 g/cm$^3$ to about 0.07 g/cm$^3$.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information on certain foam or sponge form materials, reference can be made, for example, to U.S. Pat. App. Pub. No. 2003/0013989.

In additional embodiments, occlusion devices of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM'S. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of occlusive devices. Methods for preparing such occlusive devices can include contacting an ECM or other collagenous starting material with an alkaline substance in an amount effective to expand the material, casting or otherwise forming the expanded collagenous material into an occlusive shape (e.g. an elongate tube or cylinder), and lyophilizing the expanded material to form a dried occlusive device.

Turning now to a more detailed discussion of flowable occlusive materials for use in aspects of the invention, such flowable materials can include any suitable biocompatible flowable material that will promote the closure of a venous vessel. For example, a flowable extracellular matrix material can be used to fill bodily vessels and promote tissue ingrowth to close the vessels. In this regard, the flowable material can be delivered in any suitable fashion, including for example forcible ejection from cannulated members such as catheters, sheaths, or needles. Suitable flowable, remodelable ECM materials for use in these aspects of the invention can be prepared, for example, as described in U.S. Pat. Nos. 5,275,826, 5,516,533, 6,206,931, 6,444,229 and/or in International Publication No. WO2005020847 (Cook Biotech Incorporated) published Mar. 10, 2005, which are each hereby incorporated by reference in their entirety.

Such flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth. Flowable ECM materials can also be used in conjunction with other occlusive devices as described herein, or otherwise.

For example, a flowable material can be emplaced with a formed occlusive construct, such as to help seal any voids between the construct and a vessel wall or to provide a cap at one or both device ends. Additionally, flowable material, optionally containing agents (as discussed herein), may be emplaced in between two or more other occlusive constructs to fill any desired amount of vessel space between the formed devices. Still additionally, one or more agents (or a solution thereof) can be placed in between two or more occlusive constructs (including a bolus of flowable ECM material) in a common bodily vessel to promote occlusion thereof. For more information concerning the emplacement of occlusive materials, reference can be made, for example to U.S. Pat. No. 5,456,693, which is hereby incorporated herein by reference.

Turning now to a discussion of certain synthetic materials, such as fabrics, that can be formed or incorporated into occlusive constructs for use in embodiments of the invention, such synthetic materials may include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof. Illustrative resorbable synthetic materials can include polylactic acid, polyglycolic acid or copolymers thereof, a polyanhydride, polycaprolactone, polyhydroxy-butyrate valerate, polyhydroxyalkanoate, or another biodegradable polymer or mixture thereof. For further information concerning suitable synthetic materials (both biodegradable and nonbiodegradable), useful in certain embodiments of the invention, reference can be made, for example, to U.S. Utility Pat. App. No. 2005/0228486 entitled, "Implantable Frame with Variable Compliance," filed on Apr. 11, 2005.

Turning now to a discussion of certain agents that can be conjunctively or cooperatively used with occlusive materials to provide for the closure of bodily vessels, such agents can include any substance that is capable of bringing about or inducing constriction, spasm, or closure in a bodily vessel of a patient and/or causing the de-epithelialization or inflammation (either dilative or constrictive), and/or initiating a healing response in certain patient tissue, such as a wall segment of a venous vessel. Illustrative such agents can include any suitable vasoconstrictive agent, sclerosive agent, thrombogenic agent, inflammatory agent, hypercoagulable agent, or any suitable combination of one or more of any of the above or other suitable agents. For example, suitable vasoconstrictive agents can include any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, polidocanol, sodium tetradecyl sulfate, e.g. SOTRADECOL®, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOLVE®, manufactured by Provensis, Ltd. of London, England, or any other suitable agent as disclosed in U.S. Pat. Nos. 5,676,962 and/or 6,572,873, for example, each of which is hereby incorporated herein in its entirety.

Turning now to a general discussion of occlusive constructs useful in embodiments of the invention and certain methods for making and using the same, illustrative such devices can include any material, expandable or non, that occupies a volumetric shape or space that is suitable for promoting closure of a vascular or other bodily vessel. Illustratively, such occlusive devices can include one or more boluses of a flowable remodelable material placed within a bodily lumen and/or an elongate sponge form material and/or any other suitable volumetric construct, such as can be formed by folding or rolling, or otherwise overlaying one or more portions of a biocompatible sheet material, for example. As discussed below, in embodiments, the overlaid sheet material or only portions or segments thereof, can be compressed and dried or otherwise bonded such that an occlusive construct, e.g. a substantially unitary construct, is formed. The occlusive construct can then be placed within a vascular vessel in a manner such that the construct fills at least a luminal segment of the vessel.

Occlusive constructs can include multilaminate materials, such as sheet form material or volumetric constructs formed from such multilaminate materials. To form a multilaminate construct, two or more ECM segments can be rolled or stacked, or one ECM segment folded over itself at least one time, and then the layers can be fused or bonded together using a bonding technique, such as chemical cross-linking or vacuum pressing during dehydrating conditions.

An adhesive, glue or other bonding agent may also be used in achieving a bond between ECM layers. Suitable bonding agents may include, for example, collagen gels or pastes, gelatin, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents, including those others identified in the discussions above. Cross-linking of ECM materials can also be catalyzed by exposing the matrix to UV radiation, by treating the collagen-based matrix with enzymes such as transglutaminase and lysyl oxidase, and by photocross-linking. The combination of one or more of these with dehydration-induced bonding may also be used.

A variety of dehydration-induced bonding methods can be used to fuse ECM portions of the bioremodelable material. In one preferred embodiment, the multiple layers of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In additional embodiments, illustrative occlusive constructs of the invention can be formed by randomly or regularly packing one or more pieces of single or multilayer ECM sheet material within a mold and thereafter processing the packed material. Such suitable processing can include, for example, providing the packed ECM sheet material in a partially or otherwise completely wetted or hydrated form and can complete, at least in part, by partially or completely dehydrothermally bonding the hydrated packed sheet material to establish a substantially unitary construct. Illustratively, for example, a randomly packed construct can be formed by placing folded, wadded, gathered, or otherwise packed ECM sheet material within a mold, and thereafter drying the randomly configured material to form a substantially unitary occlusive construct.

Packed, molded graft constructs can also include suitable flowable, comminuted, and/or sponge form materials, each of which can be ECM based, interspersed within rolled, folded, or otherwise randomly packed and/or covered ECM material. Additionally, these materials can be formed into any suitable shape, configuration, size and/or length as disclosed herein.

Illustratively, such cast occlusive constructs may include one or more surface protuberances and/or perforations. Such protuberances may include a plurality of such protuberances axially aligned on the surface at one or more locations, e.g. two. Such protuberances may correspond with apertures in the mold used to form the occlusive construct, such procedures typically including a drying or bonding step, e.g. lyophilization. Such perforations will typically at least partially penetrate a transverse length of occlusive construct's body, and in certain embodiments will completely transversely penetrate the occlusive constructs body. Such perforations may form a plurality of surface apertures on the construct, which may be axially aligned at one or more locations, e.g. two, and in certain embodiments such apertures can correspond with at least a portion of such protuberances. Such perforations may be initially formed as part of the process of making the occlusive constructs, such as prior to or during a drying step, e.g. lyophilization, and as such, certain segments of the perforated tract may close as the manufacture of the product completes. For more information regarding volumetric constructs, as well as surface protuberances and body apertures, reference can be made, for example, to U.S. patent application Ser. No. 11/415,403, entitled "VOLUMETRIC GRAFTS FOR THE TREATMENT OF FISTULAE AND RELATED METHODS AND SYSTEMS," filed May 1, 2006, which is hereby incorporated by reference in its entirety.

Occlusive devices for use in aspects of the invention may include any occlusive device that is pushable or guidable through a bodily vessel or bodily lumen as discussed herein and that will close or occlude the vessel after implantation. Illustrative such devices can occupy any suitable volumetric shape, form, size, and material. Such devices can include single or multilaminate sheet material, such as in a fan folded configuration that can be delivered and deployed at an implantation site in a folded over, such as folded in half lengthwise, configuration. Additional such guidable devices can include elongate sponge form devices that can be delivered and deployed in a folded-over, such as folded in half over a deployment device, or non-folded configuration. Illustrative such self guidable devices can include an expandable sponge form material having sufficient column strength such that it is advancable through a vein or other vascular vessel. Alternative such self-guidable devices can include a sheet material that is processed to itself such that it provides sufficient stiffness to the material to be advancable through a vein or other bodily vessel, or a material that incorporates certain rigid or semi-rigid materials or objects that enhance the stiffness of the occlusive material to make the material guidable through a bodily lumen.

In this regard, suitable such self guidable devices can include occlusive devices that exhibit a column strength, such as described herein, that includes any value between about 200 kPA or less to about 12,000 kPA or more. Additional such column strengths can include any value within the range of from about 700 kPA to about 11,000 kPA, and still additional such column strengths may include any value from about 1,000 kPA to about 10,000 kPA. Illustrative such column strength values can be measured using an Instron compressive strength testing machine. A sample of occlusive material, 5 cm in length, can be secured between to two test fixtures such that 0.5 cm of material is held within in each fixture. This test assembly results in a span of 4 cm of occlusive material between each fixture face. Thereafter, the fixtured sample can be placed in the Instron testing machine and compressed at a rate of 30 mm/min until the sample buckles. The force recorded at the point of buckling is the column strength or pushability number of the occlusive material.

In one preparative example, three segments of oxidized foam material, made from small intestine submucosa, each having a pre-compressed diameter of 16 mm and a length of 5 cm where compressed down to a diameter of 4 mm using a radial compression machine. Thereafter the column strength of each sample was individually determined using an Instron compressive strength testing machine. Each test was executed by securing 0.5 cm of each end of each sample within a test fixture such that a span of 4 cm of compressed foam material extended between the faces of the fixtures. The fixed sample was then compressed by the Instron machine at a rate of 30 mm/min and the compressive force was recorded. The compressive force at the point each test sample buckled was recorded as the column strength or pushability number for each sample. The column strength for each oxidized foam sample was determined to be 1488.5 kPA, 1849.6 kPA, and 1628.8 kPA, respectively.

Occlusion materials will generally be of sufficient character and/or dimension to achieve occlusion of the desired stretch of vascular vessel, either alone or in combination with other similar or differing devices. In certain embodiments, the occlusion device (or implanted flowable material) will have a length of at least about 10 cm, and in many situations at least about 20 cm. Indeed, for preferred occlusion procedures involving a significant stretch of an artery or vein, occlusion devices having lengths greater than 20 cm will be used. Illustratively, in the occlusion of the greater saphenous vein in human adolescents or adults, occlusion devices having lengths of at about 40 cm or 50 cm can be used. For more information regarding occlusive materials and methods for manufacturing the same, reference can be made, for example to U.S. Pat./App. No. 2003/0051735, U.S. Pat. No. 6,444, 229, and/or International App. Pub. Nos. WO2004/103187, WO2005/053547, and/or WO2005/020847.

Turning now to a discussion of illustrative medical products and procedures of the invention, the sclerosive or other agents can be conjunctively used with one or more occlusive devices or materials during a percutaneous ablation procedure. For example, in certain embodiments, the sclerosive agents and occlusive material can be provided separately and mixed or cooperatively implanted within a patient during an occlusion procedure. Such cooperative emplacement can include injecting or infusing one or more agents within a venous vessel before, during, or after implantation of a remodelable material, such as an elongate sponge form material. Alternatively, such conjunctive placement can include contacting a remodelable material with a sclerosive agent soon before the remodelable material is implanted within a patient, such as by soaking the remodelable material in a bath containing sclerosive agents. In sill alternative embodiments, one or more sclerosants can be mixed within a flowable ECM material before the material is injected (via syringe) or infused (percutaneously via a catheter) within a venous vessel. The agents can be mixed within the flowable material in preparation for an ablation procedure, or during the manufacture of the flowable material (such as by forming the flowable material from an ECM graft material that contains one or more sclerosive agents).

Illustratively, the sclerosive agents may be contained within the occlusive material in any suitable concentration to bring about a healing response, spasm, constriction, and/or a de-epithelielization in patient tissue that is in contact with or near the implant location. In embodiments, such as when a sclerosive solution is directly placed within a patient, the sclerosive agent can be carried within an aqueous carrier solution, such as water, saline, and the like. Illustratively, the concentration of sclerosant in the solution is from about 0.1 volume % to about 10 volume % or greater. In some embodiments the water or saline can contain from about 2 to about 4 volume % physiologically acceptable alcohol, e.g. ethanol. Saline can also be buffered, e.g. phosphate buffered. The pH of the buffer can be adjusted to be physiological, e.g. from pH 6.0 to pH 8.0, more preferably about pH 7.0.

Sclerosants may also contain additional components, such as stabilizing agents, e.g. foam stabilizing agents, such as glycerol. Further components may include alcohols, such as ethanol. For more information regarding sclerosive agents, which may be useful in certain embodiments of the present invention, reference can be made, for example, to U.S. Pat. No. 6,572,873, which is hereby incorporated by reference in its entirety.

The concentration of agent used in illustrative occlusive procedures can be varied depending, for example, on the amount of vessel dilation and/or the type of cooperative emplacement procedure techniques and devices as can be selected by the physician. Additionally, when doping an agent into an occlusive construct, higher agent concentrations may be initially used to impart the agent into the construct than will be present within or effectively delivered to the patient at or after implantation.

Illustrative dry occlusive products can be formed that contain one or more sclerosive or other agents throughout one or more regions of the construct or within or on one or more surfaces of the construct. Illustratively, such sclerosive agents can be evenly dispersed throughout the construct, or, alternatively, can be differentially concentrated throughout differing regions or surfaces of the construct, such as for example to form an occlusive construct having higher sclerosive agent concentrations at surface areas while having reduced or diminished sclerosive concentrations at core or inner areas. Such dry form ECM occluders can serve to continually deliver sclerosive agents into patient tissue after implantation so as to enhance occlusion and remodeling of the occlusive device. Such occlusive devices can be deployed in dry form within a patient and thereafter optionally hydrated with a suitable hydrant, e.g. saline, or in alternative embodiments can be hydrated before implantation occurs.

Illustrative dry occlusive devices can be formed by contacting an occlusive material with one or more sclerosing agents and thereafter drying the material so as to form a dry occlusive material that is doped with or otherwise contains sclerosive agents. For example, an ECM sheet material can be soaked within a bath containing a sclerosive agent and can thereafter be rolled and pressed into a mold and thereafter lyophilized (freeze dried) so as to form a substantially unitary occlusive construct containing sclerosive agents. If desirable, such as when the occlusive construct comprises a sponge form ECM material, the construct can be compressed or recompressed after lyophilization is complete.

While discussions above focus upon occluding the greater saphenous vein via access at the knee level, the greater saphenous vein may also be accessed at a higher, e.g. jugular or lower level, e.g. near the ankle. During such access, any or all of the saphenous vein occurring between the ankle and the sapheno-femoral junction may be subjected to occlusion. Other veins in the leg(s) that may be involved in the varicose vein condition, e.g. spider veins, may also be occluded, alternatively or in addition to the saphenous vein. For example, the lesser saphenous vein, or varicose veins themselves, may be occluded and obliterated in accordance with the invention. Further, other veins or arteries in the leg(s) or elsewhere in the body may be occluded within the scope of the present invention.

Percutaneously-conducted occlusion procedures can be performed under local anesthesia. In addition, after completion of the procedure, it may be beneficial to use graduated compression stockings in the occluded area, for example for a week or more. Compression of the occluded area may serve to facilitate permanent closure of the occluded vessel, for example when applied during a remodeling period during which tissue ingrowth into the occluded lumen occurs.

Sheaths, dilators, pushers, wire guides and needles used in the present invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators and pushers can be made from conventional dilator/catheter type materials such as polyethylene, polyamide, stainless steel, polyurethane or vinyl, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Delivery sheaths used in the invention will have a lumen diameter sized to allow for the introduction of a sufficient amount of occlusion material to occlude the artery or vein of interest. Illustratively, the inner diameter (I.D.) of the final delivery sheath can range from about 4 French up to about 40 French.

As is conventional, the distal ends of the catheters, sheaths, dilators, wires or other components, e.g. occlusive constructs, used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on occluder devices of the invention may include markers for non-invasive imaging, including imageable materials such as those discussed above as well as substances that can be applied to ECMs or other collagenous materials, e.g. substances containing tantalum, barium, iodine, or bismuth, e.g. in powder form.

The invention also provides medical kits that include medical products described herein sealed within medical packaging potentially in combination with other components, such as for example a sheath and/or guidewire. The final, packaged products are provided in a sterile condition. This may be achieved, for example, by gamma, e-beam or other irradiation techniques, ethylene oxide gas, or any other suitable sterilization technique, and the materials and other properties of the medical packaging will be selected accordingly.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical product for occluding a venous vessel, comprising:
an occlusive construct comprising a remodelable material configured for deployment within a venous vessel to fill at least a luminal segment of the venous vessel so as to occlude the venous vessel, wherein the remodelable material is a dried collagenous extracellular matrix material harvested to retain and retaining bioactive components native to a source tissue for the dried collagenous extracellular matrix material and which is effective to induce angiogenesis when deployed within the vessel, wherein the dried collagenous extracellular matrix material is effective to promote the ingrowth of patient tissue into the lumen of the venous vessel and lead to angiogenesis and wherein the occlusive construct includes one or more dried sclerosants that are effective to injure the lining of the venous vessel so as to enhance the ingrowth of patient tissue into the occlusive construct and promote occlusion of the venous vessel, the dried collagenous extracellular matrix material comprising at least 80% by weight collagen on a dry weight basis, including uniaxial or multiaxial oriented fibers, and including at least about 3% retained non-collagenous solids from the source tissue, the non-collagenous solids including said bioactive components.

2. The medical product of claim 1, wherein the one or more dried sclerosants comprises sodium tetradecyl sulfate, morrhuate sodium, ethanolamine oleate, tetradecyl sulfate, tetracycline, glycerin, hypertonic glucose, talc, acetic acid, alcohol, bleomycin, picibanil, ethibloc, deoxycycline polidocanol, sotradecol, ethoxysclerol, or any suitable mixture thereof.

3. The medical product of claim 1, wherein the one or more dried sclerosants comprises sodium tetradecyl sulfate, morrhuate sodium, ethanolamine oleate, tetradecyl sulfate, tetracycline, glycerin, hypertonic glucose, talc, acetic acid, alcohol, bleomycin, picibanil, ethibloc, deoxycycline polidocanol, sotradecol, ethoxysclerol, or any suitable mixture thereof.

4. The medical product of claim 1, wherein the one or more dried sclerosants comprise polidocanol or sodium tetradecyl sulfate.

5. The medical product of claim 1, wherein the collagenous extracellular matrix material comprises a sponge form material.

6. A medical product for occluding a bodily vessel, comprising:
an angiogenic remodelable collagenous extracellular matrix material constituted of at least 80% collagen, the extracellular matrix material harvested to retain and retaining non-collagen solids from a source tissue for the extracellular matrix material, wherein the non-collagen solids comprise native bioactive factors from the source tissue, wherein the angiogenic remodelable collagenous extracellular matrix material is dried and is configured for deployment in a bodily vessel of a patient; and one or more dried sclerosing agents, wherein the dried sclerosing agents and the remodelable collagenous extracellular matrix material are configured for conjunctive or cooperative use to enhance closure of the bodily vessel.

7. The medical product of claim 6, wherein the one or more dried sclerosing agents are located within the angiogenic remodelable collagenous extracellular matrix material.

8. The medical product of claim 7, wherein the angiogenic remodelable collagenous extracellular matrix material comprises a sponge form or foam material.

9. The medical product of claim 8, wherein the bioactive factors comprise growth factors.

10. The medical product of claim 8, wherein the one or more dried sclerosing agents comprises sodium tetradecyl sulfate, morrhuate sodium, ethanolamine oleate, tetradecyl sulfate, tetracycline, glycerin, hypertonic glucose, talc, acetic acid, alcohol, bleomycin, picibanil, ethibloc, deoxycycline polidocanol, sotradecol, ethoxysclerol, or any suitable mixture thereof.

11. The medical product of claim 6, wherein the angiogenic remodelable collagenous extracellular matrix material comprises an extracellular matrix sheet material.

12. The medical product of claim 11, wherein the sheet material is folded.

13. The medical product of claim 12, wherein the sheet material is fan folded.

14. The medical product of claim 11, wherein the sheet material is rolled to form a cylindrical body of overlapping or layered sheet material.

15. The medical product of claim 14, wherein the overlapping layers are dehydrothermally bonded.

16. A medical product, comprising:
a dry, implantable occlusive construct including a dried, bioactive remodelable extracellular matrix material with one or more dried sclerosants incorporated in the dried, bioactive remodelable extracellular matrix material, the occlusive construct configured for deployment within a venous vessel to fill at least a luminal segment of the venous vessel so as to occlude the venous vessel, wherein the dried, bioactive remodelable extracellular matrix material retains bioactive components native to a source tissue for the remodelable extracellular matrix material and is effective to induce cellular invasion and the ingrowth of patient tissue into the lumen of the venous vessel and to induce angiogenesis when deployed within the vessel, the one or more dried sclerosants being effective to injure the lining of the venous vessel so as to enhance the ingrowth of patient tissue into the occlusive construct and promote occlusion of the venous vessel.

17. The medical product of claim 16, wherein the extracellular matrix material comprises at least 80% by weight collagen on a dry weight basis, includes uniaxial or multiaxial oriented fibers, and includes at least about 3% retained non-collagenous solids from the source tissue, the non-collagenous solids including said bioactive components.

18. The medical product of claim 17, wherein the extracellular matrix material comprises submucosa, serosa, pericardium, dura mater, peritoneum, or basement membrane.

19. The medical product of claim 18, wherein the submucosa comprises mammalian submucosa.

20. The medical product of claim 19, wherein the mammalian submucosa comprises porcine, bovine, or ovine submucosa.

21. The medical product of claim 19, wherein the mammalian submucosa comprises intestine submucosa, stomach submucosa, urinary bladder submucosa, or uterine submucosa.

22. The medical product of claim 21, wherein the intestine submucosa comprises adult porcine small intestine submucosa.

23. The medical product of claim 17, wherein the bioactive components comprises growth factors.

24. The medical product of claim 23, wherein the one or more dried sclerosants comprise morrhuate sodium.

25. The medical product of claim 24, wherein the one or more dried sclerosants comprise polidocanol or sodium tetradecyl sulfate.

26. The medical product of claim 25, wherein the one or more dried sclerosants comprise polidocanol.

27. The medical product of claim 16, wherein the remodelable extracellular matrix material comprises a sponge form material.

* * * * *